United States Patent [19]

Boothroyd

[11] Patent Number: 4,581,491

[45] Date of Patent: Apr. 8, 1986

[54] WEARABLE TACTILE SENSORY AID PROVIDING INFORMATION ON VOICE PITCH AND INTONATION PATTERNS

[75] Inventor: Arthur Boothroyd, New York, N.Y.

[73] Assignee: Research Corporation, New York, N.Y.

[21] Appl. No.: 607,077

[22] Filed: May 4, 1984

[51] Int. Cl.[4] ...................... H04R 25/00; G08B 1/00; G09B 21/00

[52] U.S. Cl. ............................ 179/107 FD; 340/407; 381/68; 434/114

[58] Field of Search .................... 179/107 FD, 107 R; 381/68, 69; 434/113, 114; 340/407

[56] References Cited

U.S. PATENT DOCUMENTS

| | | | |
|---|---|---|---|
| 4,025,732 | 5/1977 | Traunmüller | 179/107 FD |
| 4,250,637 | 2/1981 | Scott | 340/407 |
| 4,354,064 | 10/1982 | Scott | 179/107 FD |

FOREIGN PATENT DOCUMENTS 3003315  8/1981  Fed. Rep. of Germany ...... 179/107 FD

OTHER PUBLICATIONS

"A Portable Tactile Aid . . . " by Allen Katz et al, *Proceedings of Seventh New England Bioengineering Conf.*, Mar. 1979.

"Inventor Tries to Perfect Tactile Speech . . . ", Gross, *Washington Post*, Oct. 11, 1982, p. 5.

*Primary Examiner*—Gene Z. Rubinson
*Assistant Examiner*—Danita R. Byrd
*Attorney, Agent, or Firm*—Scully, Scott, Murphy & Presser

[57] ABSTRACT

A wearable tactile sensory aid which presents a vibratory signal representative of voice pitch and intonation patterns to the skin. The vibratory signal consists of a constant amplitude square wave having a frequency equal to, or some fraction of, the fundamental frequency of the speech input. The vibratory signal is applied as a tactile stimulus, and is displaced along a linear array of transducers in contact with the skin in proportion to the logarithm of the fundamental frequency. Accordingly, the wearable tactile display encodes the fundamental frequency to provide both frequency of actuation and spatial indications thereof.

10 Claims, 6 Drawing Figures

FIG.2 - PITCH EXTRACTOR 14

FIG.4-FREQUENCY METER 24

WEARABLE TACTILE SENSORY AID PROVIDING INFORMATION ON VOICE PITCH AND INTONATION PATTERNS

BACKGROUND OF THE INVENTION

1. Field of the Invention

The present invention relates generally to a wearable tactile sensory aid for deaf persons, and more particularly pertains to a portable tactile sensory aid designed to be worn by profoundly or totally deaf individuals which provides them with information on voice fundamental frequency which is simultaneously encoded to provide both frequency of actuation and spatial indications thereof.

2. Discussion of the Prior Art

The prior art provides an extensive history on tactile sensory aids for the deaf. When wearable, such devices have typically been implemented as single channel devices. In general, these sensory aids are designed to provide deaf persons with access, via the sense of touch, to the acoustic waveform of speech.

Intonation patterns, i.e., the patterns of variation in the fundamental frequency of the voice over time, play several roles in speech. For example, they help define where sentences begin and end, they mark the more important words in a sentence, and they sometimes serve to differentiate questions from statements. The expected benefits of a wearable tactile intonation display to a deaf individual are faster and more accurate lipreading and improvements in the quality and intelligibility of self-generated speech. Although intonation information is not accessible by lipreading, many deaf persons have sufficient residual hearing for the perception of intonation when using hearing aids. The present invention is not generally intended for those partially deaf persons, but for those deaf persons whose hearing is so badly damaged that hearing aids are either useless, or, at best, provide access only to patterns of variation in amplitude over time.

There is a long history in the prior art of attempts to alleviate the problems of deafness by converting the sounds, movements, or airflow characteristics of speech into patterns that can be perceived via the undamaged senses of vision or touch. Regarding the tactile representation of intonation patterns, the simplest way to convey acoustical information through the sense of touch is to amplify the speech waveform and feed it to a single electromechanical transducer that is in contact with the skin. A single channel device of this type was first described in the prior art in the 1920s. A more modern version of this early single channel is presently commercially available as the Siemens Monofonator, which is a desk-top unit.

Wearable single channel devices that employ mechanical transduction of the acoustic waveform have also been described in the prior art. In addition, it has been pointed out that for the totally deaf individual, a high power hearing aid can serve, in effect, as a wearable, single channel, tactile stimulator.

Experiments on the psychophysics of the sense of touch have shown that there should be sufficient frequency discrimination to provide at least partial access to intonation patterns. Evaluation of the single channel tactile devices mentioned above, however, has failed to provide evidence that they serve to provide information on intonation. Instead, their benefits appear to be limited to perception of the amplitude envelope of the speech signal.

It is possible to provide information on intonation in a single channel display by suitable forms of signal processing. However an alternative approach also exists in representing fundamental frequency as a position of vibratory stimulation using an array of transducers. The changes of frequency that constitute intonation then become encoded as movements of tactile sensation, thereby acquiring considerable perceptual salience. A display of this type using only the encoded position within an array was developed in the early 1970s and was used in a promising evaluative study with deaf children. However, this was a desk-top unit, and could only be used for brief periods of one-to-one instruction.

SUMMARY OF THE INVENTION

Accordingly, in view of the aforementioned shortcomings of the prior art, it is a primary object of the present invention to provide an improved wearable tactile sensory aid designed to extract fundamental frequency from a speech signal and to represent it as the locus of pitch-synchronous, vibratory stimulation of the skin.

The present invention is designed to provide profoundly or totally deaf individuals with access to the information contained in the fundamental frequency of the voice. This information, which cannot be perceived by lipreading, plays an important role in defining sentence and phrase boundaries, in marking stressed words, and in distinguishing among certain speech sound categories (e.g., p and b). The device should therefore be of assistance to the congenitally deaf in the acquisition of speech skills, and to all deaf individuals by improving speech perception and self-monitoring.

Further objects of the present invention are to provide a portable, wearable tactile sensory aid which provides a tactile presentation of the fundamental frequency of speech by a simultaneous encoding of the fundamental frequency to provide both frequency of actuation and spatial indications thereof.

In accordance with the teachings herein, the present invention provides a tactile sensory aid designed to be worn by a deaf person for detecting and providing to that person tactile information on the fundamental frequency of detected speech, encoded in both the temporal and spatial domains. The tactile sensory aid includes a transducer, such as a microphone or accelerometer, for detecting speech and providing an output speech signal indicative thereof. A pitch extractor analyzing circuit analyzes the speech signal and provides an output signal representative of the fundamental frequency of the detected speech. A transducer array is designed to be attached to a tactile-sensitive area of the deaf person's body. The transducer array defines a geometrical array, such as a linear array, such that the activation of a particular transducer in the geometrical array provides a spatial indication to the person of the detected fundamental speech frequency. A frequency metering circuit analyzes the output signal to detect the fundamental frequency, and energizes a particular transducer in the transducer array, in dependence upon the detected fundamental frequency, with a signal representative of the fundamental speech frequency. In this arrangement the frequency of actuation of the transducer provides an indication of the fundamental speech frequency, while the location of the particular transducer in the geometric array simultaneously provides a spatial indication of the fundamental speech frequency.

In greater detail, the frequency metering circuit energizes a particular transducer in the transducer array in dependence upon the logarithm of the fundamental frequency. The frequency metering circuit provides a periodic output signal representative of the fundamental frequency. Each cycle of the periodic signal has first and second portions, and the frequency analyzing means times the first portion of each cycle to determine the frequency of the periodic output signal, and thereby which transducer in the transducer array is to be activated, and then drives the activated transducer with the second portion of each cycle of the periodic waveform. The frequency analyzing circuit includes a shift register having a separate register output for each transducer in the transducer array. The register is driven by an internal clock, and the pitch extractor circuit produces a square wave output signal at the detected fundamental frequency. Essentially, the shift register measures the "off" portion of the square wave output signal and directs the "on" portion of the square wave output signal to a particular transducer in accordance with the measured "off" portion which is indicative of its frequency.

In accordance with another novel aspect of the present invention, the portable transducer array is designed to rely upon the resiliency of the skin of the person wearing the array to provide a restoring force for each transducer. Moreover, the preferred embodiment of the tactile sensory aid is designed to be portable, and thereby requires a rechargeable portable battery power supply, to be carried by the person, for providing electrical power for all of the various circuits forming components thereof.

Moreover, a preferred embodiment of the present invention should also have the following desirable attributes: be small and light enough for continuous use without discomfort or inconvenience; the output transducer should be capable of being worn where it does not interfere with the activities of daily living; be operated from rechargable batteries with enough capacity for a full day's usage between charges; respond both to self-generated speech and to the speech of other talkers up to fifteen or twenty feet distant (e.g., classroom teacher); respond to the speech of men, women and children without readjustment of circuit parameters (this is a demanding criterion since the fundamental frequency of an adult male voice can drop as low as 70 Hz while that of a young child can rise as high as 600 Hz); respond rapidly enough to provide an output from unstressed syllables which can be as short as 70 milliseconds; lateral displacement of the tactile output should be proportional to the logarithm of the fundamental frequency (this requirement derives from the fact that frequency ratios within an intonation contour remain constant as the average frequency changes); the output transducer array should provide one channel resolution, and the generated tactile patterns should permit discrimination among the major types of speech intonation contour.

BRIEF DESCRIPTION OF THE DRAWINGS

The foregoing objects and advantages of the present invention for a portable tactile sensory aid may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
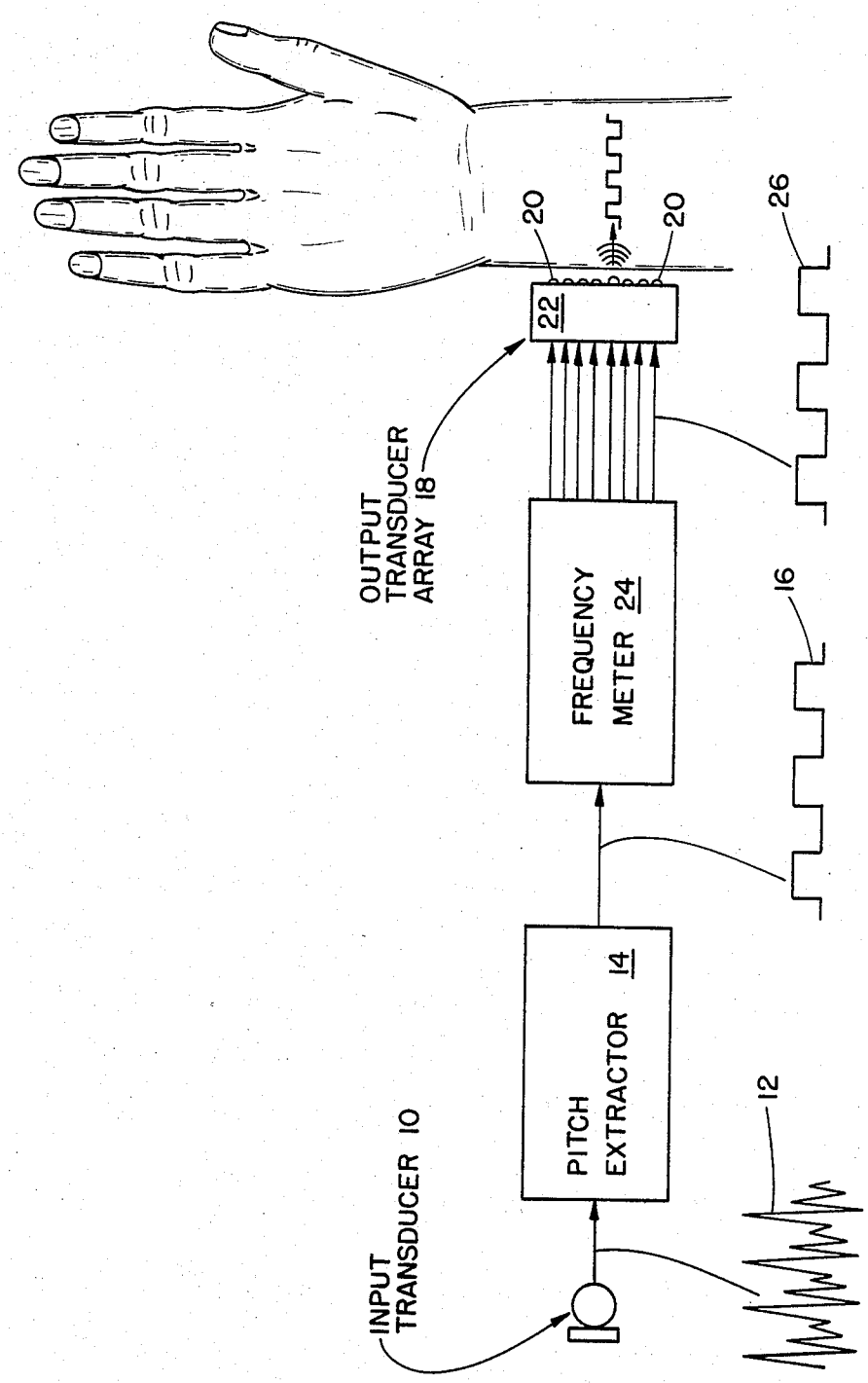
FIG. 1 is a block diagram of an exemplary embodiment of a portable tactile sensory aid constructed pursuant to the teachings of the present invention.

Referring to the drawings in detail, FIG. 1 illustrates a block diagram of a first exemplary embodiment of a portable tactile sensory aid constructed pursuant to the teachings of the subject invention. In this embodiment, an input detecting transducer 10, such as a microphone or an accelerometer, detects input speech sounds and provides an output analog electrical speech signal 12 indicative thereof. A fundamental frequency pitch extractor circuit 14 receives the analog speech signal as an input, and uses a combination of low-pass filtering and peak detection to generate a square wave output signal 16 representative of the fundamental frequency of the detected speech. In the disclosed embodiment, the representative square wave signal has a frequency half that of the fundamental frequency of the speech signal.

A transducer array 18 is attached to a tactile-sensitive area of the body of the deaf person. The transducer array defines a geometrical array, such as a linear array, such that the activation of a particular transducer within the geometrical array provides a spatial indication to the person of the fundamental frequency of the detected speech. In one disclosed embodiment, the output transducer array 18 consists of eight miniature solenoids 20 mounted in a small plastic box 22.

A frequency meter analyzing circuit 24 receives the square wave output signal 16 representative of the fundamental frequency. This circuit detects the frequency of the square wave output signal, and energizes a particular transducer 20 in the transducer array, depending upon the detected frequency, with an output signal 26 representative of the fundamental frequency of the detected speech. In the disclosed embodiment, the frequency meter analyzing circuit uses a shift register and a clock, and the first half of each square wave cycle is timed, with the result determining which of eight output channels is actuated during the second half of each square wave signal.

In this overall arrangement, the frequency of actuation of the transducer provides an indication of the fundamental speech frequency, while the location of the particular transducer in the geometric array simultaneously provides a spatial indication of the fundamental speech frequency. The input transducer 10 can be an electret tie-clip microphone (such as RadioShack type 33-1058), which detects acoustic inputs, or it can be an accelerometer (such as a Knowles type BU-1771) to provide direct input from surface vibrations of the talker's throat. The casing of the accelerometer can be fashioned from a short piece of shrink-fit tubing.

A tie-clip microphone has an advantage of convenience but is susceptible to high ambient noise levels, especially if the talker is several feet distant. The accelerometer eliminates the ambient noise problem, and provides a signal with a strong fundamental frequency. It is more restrictive than the microphone, however, requiring attachment to the talker's skin.

In general, the pitch extraction circuitry requires a strong signal with a minimum of background noise. In educational settings and for self-monitoring, this can be provided by a contact microphone which picks up the voice signal directly from the skin of the throat. This signal can, if necessary, be transmitted to the tactile pitch display via an FM wireless link. For use with an acoustic microphone in a less than ideal acoustic environment, a high performance pitch extractor circuit would normally be required.

Figure 2:
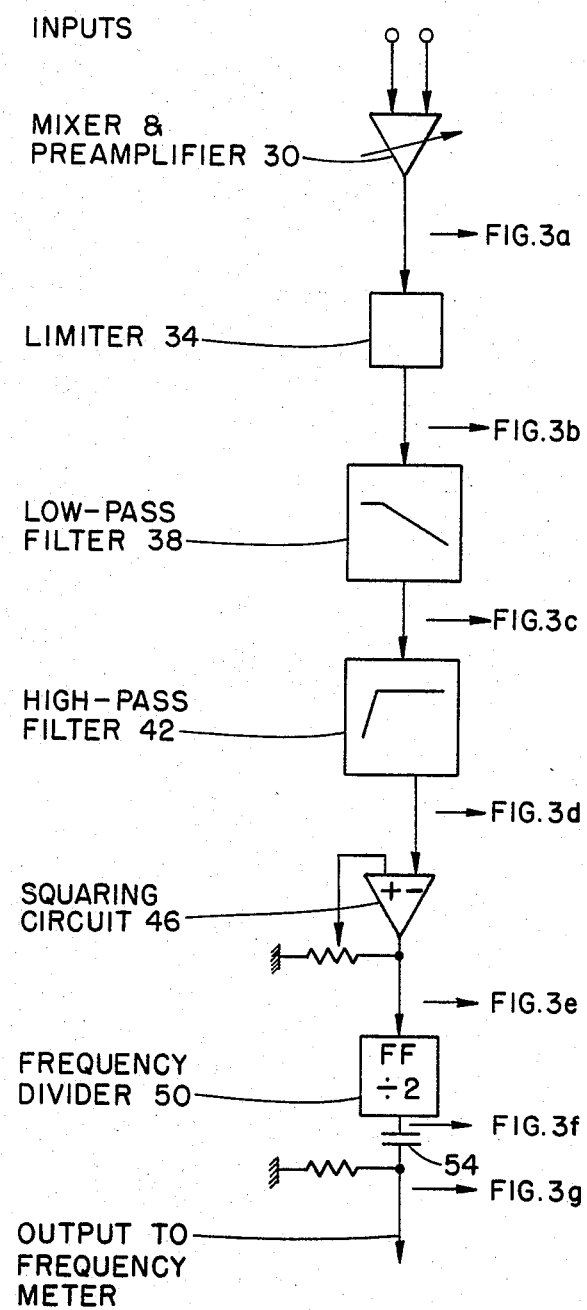
FIG. 2 illustrates an exemplary embodiment of a pitch extractor analyzer circuit according to the teachings herein.
Figure 3:
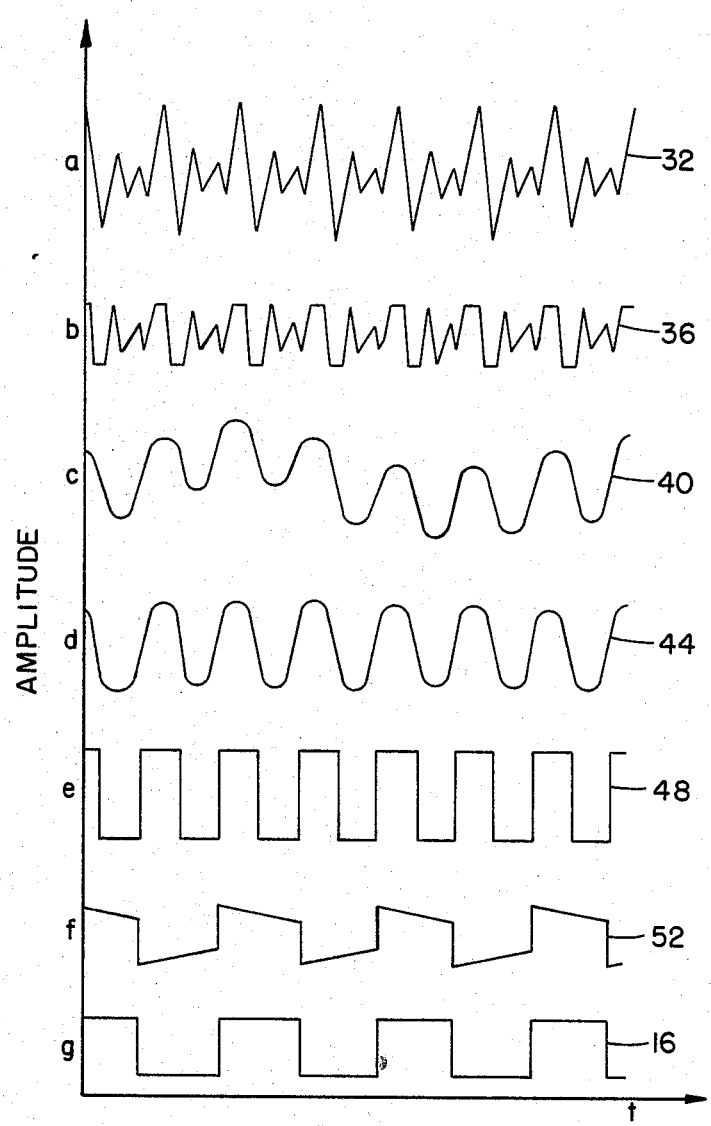
FIG. 3 illustrates waveforms associated with the pitch extractor circuit of FIG. 2 which are useful in explaining the operation thereof.

FIG. 2 illustrates a block diagram of the pitch extractor circuit 14, while FIG. 3 illustrates different waveforms associated with the circuit of FIG. 2 which are useful in explaining the operation thereof. A preamplifier 30 amplifies the input signal from the transducer 10, and the resultant amplified signal 32 is clipped by a limiting circuit 34 to increase the amplitude of the fundamental frequency through intermodulation between adjacent harmonics of voice sounds. Two inputs to the preamplifier are illustrated to provide for inputs from more than one input transducer, in which case the preamplifier also functions as a mixer. The resulting signal 36 is then low-pass filtered at 38, preferably by using four stages of R.C. filtering. By adjustment of the cut-off frequency of each stage, the slope of the composite filter can be varied between 6 and 24 dB per octave. Its cut-off frequency can be varied from below 70 Hz to above 300 Hz. The object is to operate in the skirt of this filter 38 so that the relative attenuation of the harmonics remains constant as the fundamental frequency changes. The drawback to this approach is that the absolute attenuation of the fundamental increases with increasing frequency, creating severe signal-to-noise problems in the higher frequencies.

The resultant signal 40 next passes through a high-pass filter 42 with a cut-off frequency of approximately 50 Hz. The high-pass filter attenuates low frequency noise and eliminates DC shifts. The resulting signal 44 approximates a sinusoid which is symmetrical about ground potential. This signal is then squared by a bistable level detector 46 with hysteresis to produce a square wave signal 48 having a 50% duty cycle. A flip-flop 50 is used to divide the frequency by two and to ensure that the square wave output, for a constant frequency input, has a 50% duty cycle. The frequency division is dictated by the response time of the output transducers, while the 50% duty cycle is a requirement of the frequency meter circuit 24. The output 52 of flip-flop 50 is then restored and limited to a DC square wave 16, FIGS. 1 and 3g, by AC coupling through a capacitor 54. The DC restored and limited signal 16 provides a 0-5 volt square wave input for the following stages. The output is AC coupled to the frequency meter to ensure that the voltage drops rapidly to zero if the flip-flop is left "high" at the end of a voiced speech segment.

Figure 4:
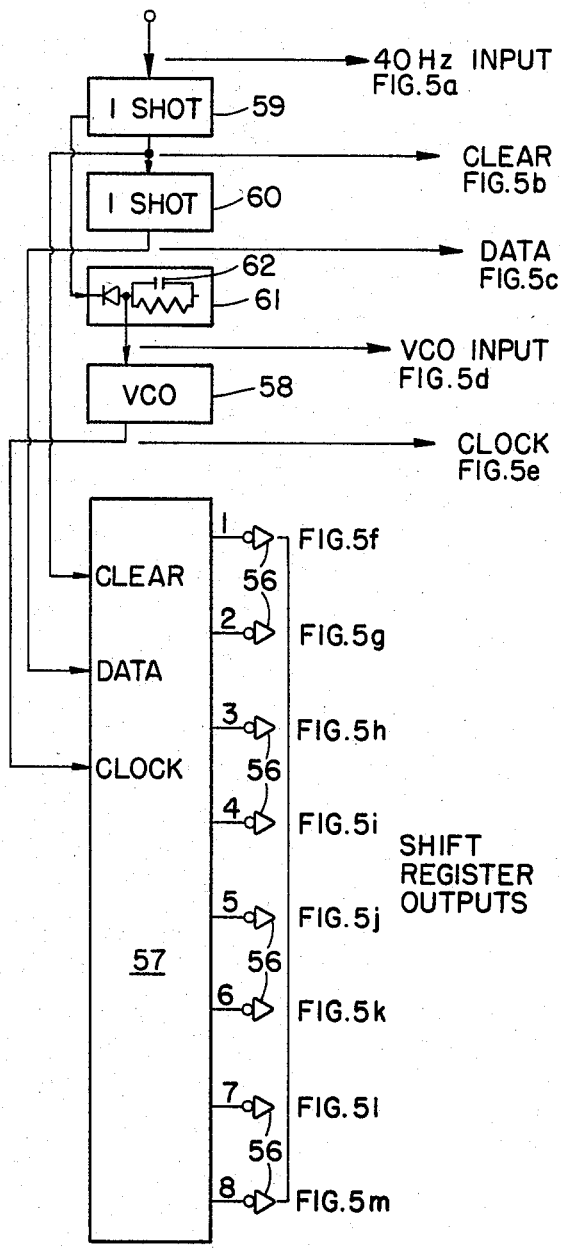
FIG. 4 is a schematic illustration of a frequency meter analyzing circuit for analyzing the square wave output signal of the pitch extractor circuit and for energizing a particular transducer in the transducer array in dependence upon the logarithm of the frequency of the square wave signal.

FIG. 4 illustrates a block diagram of the frequency meter analyzer circuit 24. To achieve the speed of response dictated by the brief durations of unstressed syllables, frequency is measured cycle by cycle as the reciprocal of the periodic time. Essentially, the frequency analyzer circuit measures or times the first half of each cycle of the incoming square wave (hence the need for 50% duty cycle), and routes the second half of each square wave cycle to the appropriate one of eight output drive transistors 56. This is accomplished by inserting a data bit, FIG. 5c, into position #1 of an eight bit shift register 57 and advancing this with an internal clock 58. The location of the bit at the end of the first half cycle determines which output transistor will be switched on during the second half.

With a fixed clock frequency, f, the upper and lower frequency limits ($F_u$ and $F_l$) of this circuit are given by:

$$F_u = 1/T$$

$$F_l = 1/(T + 8/f)$$

where T is the time from the onset of each cycle of the input square wave to the insertion of the data bit.

Unfortunately, a fixed clock frequency does not provide a desired logarithmic relationship between channel number and input frequency. To solve this problem, the clock 58 frequency is modulated with an exponential waveform, FIG. 5d, produced by a logarithmic modulator circuit 61, which exponential waveform is derived from the signal from one shot 59 used to clear the shift register. The lower frequency limit now becomes $$F_l = 1/\left(T + \sum_{n=1}^{n=8} t_n\right)$$

where $t_n$ is the period of the nth clock cycle. By suitable adjustment of the time constant of the modulation waveform, FIG. 5d, the desired logarithmic relationship between channel number (1 to 8) and input frequency is obtained.

Figure 5:
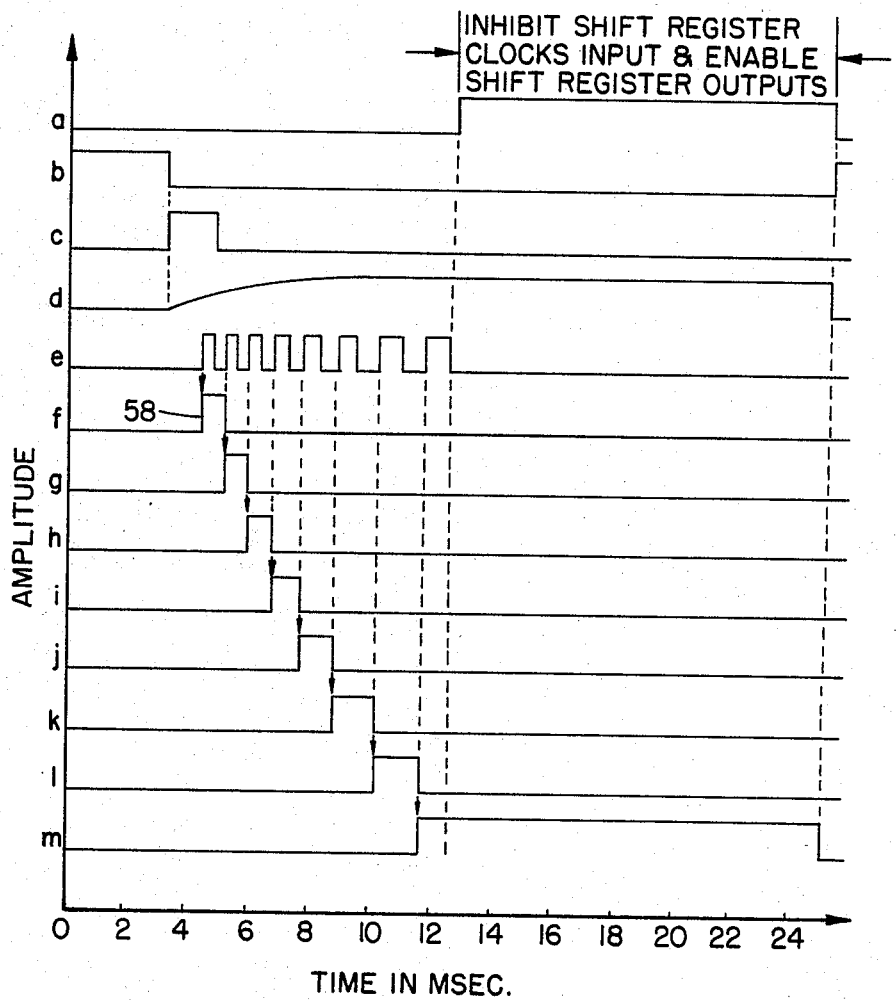
FIG. 5 illustrates waveforms associated with the frequency analyzing circuit of FIG. 4 which are useful in explaining the operation thereof.
Figure 6:
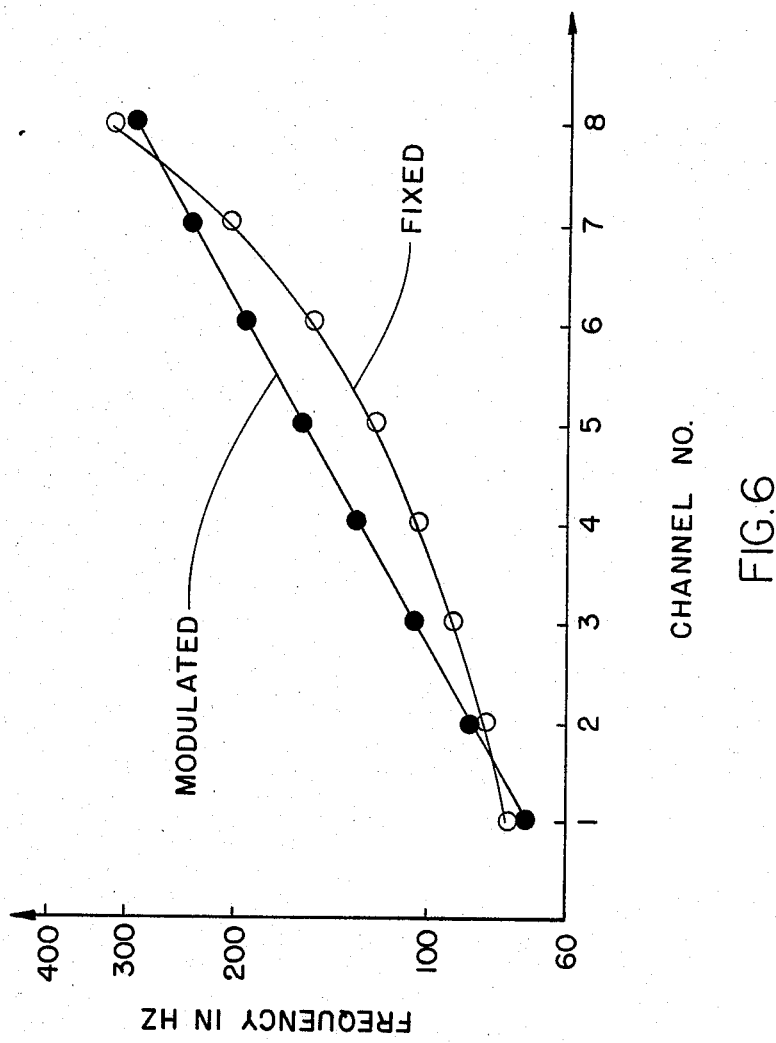
FIG. 6 illustrates graphically the effect of the logarithmic modulation function performed by the circuit of FIG. 4.

In the circuit of FIG. 4, a first one shot 59 produces a clear output signal, FIG. 5b, to clear the shift register and to trigger a second one shot 60, which produces the aforementioned data bit, FIG. 5c. The output of one shot 59 also discharges a capacitor 62 in modulator circuit 61, which then recharges from a +5 VDC power supply to produce the logarithmic waveform, FIG. 5d. The clock 58 is a voltage controlled oscillator which, under the control of exponential waveform 5d, produces the exponentially varying clock pulse train of FIG. 5e, in which the frequency of the clock pulses is modulated exponentially by the exponential waveform applied to the oscillator clock 58. When the Voltage Controlled Oscillator (VCO) 58 receives an input control voltage waveform, FIG. 5d, which varies exponentially, then the frequency of the controlled oscillator clock pulses produced thereby will also vary exponentially under control of the input waveform, as is typical for operation of a VCO. The results of this circuit are also illustrated graphically in FIG. 6.

In summary, in the pitch period timing circuitry, the shift register, driven by an internal clock, measures the duration of the "off" portion of a square wave input, and routes the "on" portion to one of eight (or more) output transducers. An exponential waveform is used to modulate the clock frequency so as to produce a spatial scaling that is proportional to the logarithm of fundamental frequency. This feature ensures that the spatial representation of intonation contours is unaffected by changes of average fundamental frequency (e.g. by the shift from a male to a female voice).

The output transducer array 18 consists of eight miniature solenoids (Electromechanisms SP-18, (6 volt)). Since the force on the armature of a solenoid increases as it is drawn into the coil, the device functions as a mechanical bistable system providing a square wave stimulus whose amplitude equals the armature stroke. For maximum efficiency, the armature stroke was reduced to 0.5 mm and a restoring spring was removed. In this configuration, the skin provides the restoring force, the magnitude of which is controlled primarily by the protrusion of the actuator tip from the surrounding surface. The use of the skin to provide the restoring force for each transducer also improves the electromechanical efficiency.

Continuous operation at a fixed frequency can cause the responding solenoid to overheat unless a heat sink is provided. In normal usage, however, the solenoids are inactive for more than 50% of the time, and the changes of frequency that occur in real speech generally ensure that the output shifts from solenoid to solenoid.

In one constructed embodiment, the solenoid array is mounted in a plastic box, with a channel spacing of ¼ inch. Hearing aid cords are used to provide flexible connection to the main electronics package, and the array is preferably attached to the forearm with leather and Velcro straps.

The electronics package, together with three NiCad batteries (two for the pitch extractor circuit and for the pitch period meter circuit, and one for the output transistors) is mounted in a plastic box 22 measuring 6×4×2 inches. This is designed to be attached to a belt. In addition to power switches and charger receptables, an external control is provided for preamplifier sensitivity. Increasing the sensitivity increases the distance from which the device will accept microphone inputs. Decreasing the sensitivity minimizes the effects of background noise.

In evaluations of the disclosed embodiment, three placements of the solenoid array were used: the base of the thumb, the side of the hand (opposite the thumb), and the side of the forearm (also opposite the thumb). In both psychophysical and speech perception experiments with normally hearing subjects, performance was best when the array was placed on the hand. Use of the arm gave only slightly inferior results, however, and it is possible that with increased solenoid spacing, even this difference may be eliminated. Placement on the forearm interferes only minimally with the activities of daily living.

The pitch extractor circuitry and frequency meter circuitry operate from two 9 volt NiCad batteries and draw 30 to 40 milliamps from each, providing only two or three hours of use between charges. It is estimated that by careful design of the electronics, with elimination of voltage regulators, the life between charges can be extended to five or six hours.

The output solenoids draw 200 milliamps when activated and presently have a separate supply. Since the output signal is a square wave, the average current drain during voicing is 100 milliamps, and since voicing is present for less than 50% of the time during use, the overall average current drain is 30 to 40 milliamps. This again provides two to three hours of use between charges of a NiCad battery, which can be improved also.

Experiments with normally hearing subjects confirmed that single channel changes of stimulus location can be detected with relative ease. It was also demonstrated that the system permits discrimination among some of the principal intonation contours of English, an advantageous factor in the rehabilitation of hearing-impaired children.

In a quiet room the system responds well to male talkers up to eight or ten feet from the microphone. With moderate ambient noise, however, or with female talkers, microphone distances of a few inches are required. Alternatively the surface accelerometer may be used. For many applications, e.g., self monitoring, or one-to-one instruction, this level of input sensitivity is adequate. If it is necessary to detect speech at a distance in a noisy environment, a wireless link may be used.

The low-pass filtering used in the pitch extractor circuit is incompatible with a frequency range of 70 to 600 Hz. Even if such a wide range were possible, the fact that there are only eight output channels would restrict the channel bandwidth to approximately ⅓ octave. This would be unlikely to provide adequate discrimination among the major types of intonation contour. With close microphone input, or accelerometer input, and careful adjustment of both the low-pass filters and the switching levels of the squaring circuit, the pitch extractor operates well over a range of 70 to 300 Hz. This provides a channel bandwidth of ¼ octave and covers the typical range of adult male and female talkers without readjustment.

Since the frequency meter is, in fact, a pitch period meter, it can respond within one cycle of the input square wave. It will be recalled that the frequency of this square wave is half the fundamental frequency of the speech input. Response time is therefore two cycles of the speech waveform. For a typical male talker, the fundamental frequency averages approximately 100 Hz, and maximum response time is therefore 20 milliseconds. Moreover, the disclosed logarithmic scaling circuit does indeed provide a logarithmic relationship between the output channels and the input frequency.

The tactile sensory aid of the present invention might possibly achieve a maximum benefit if the deaf person can wear it continuously, incorporating its output into his sensory and sensorimotor functions. The present invention provides the possible benefits of continuous access to tactually coded intonation patterns.

While several embodiments and variations of the present invention for a portable tactile sensory aid are described in detail herein, it should be apparent that the disclosure and teachings of the present invention will suggest many alternative designs to those skilled in the art. For instance, alternative circuit designs could be implemented in the pitch extractor analyzer circuit 14 and the frequency meter circuit, although perferred designs for both circuits are disclosed herein. Moreover, the output transducer array 22 could also be implemented with different designs, including different geometrical arrays, such as circular arrays, etc.

What is claimed is:

1. A tactileسهsensory aid to be worn by a deaf person for detecting and providing to the person tactile information on the fundamental frequency of detected speech, encoded to provide both frequency of actuation and spatial indications thereof, comprising:

a. a transducer for detecting speech and providing an output speech signal indicative thereof;

b. a fundamental frequency analyzing means receiving said speech signal as an input and providing an output signal representative of the fundamental frequency of the detected speech;

c. a transducer array, to be attached to a tactile-sensitive area of the body of the deaf person, said transducer array defining a geometrical array such that the activation of a particular transducer within the geometrical array provides a spatial indication to the person of the fundamental frequency of the detected speech; and d. a frequency analyzing means, receiving said output signal representative of the fundamental frequency, for detecting the frequency of the output signal of the fundamental frequency analyzing means and for energizing a particular transducer in the transducer array in dependence upon the logarithm of the fundamental frequency of the detected speech, such that the frequency of actuation of the transducer provides an indication of the fundamental speech frequency, while the location of the particular transducer in the geometric array simultaneously provides a spatial indication of the fundamental speech frequency.

2. A tactile sensory aid as claimed in claim 1, said fundamental frequency analyzing means providing a periodic output signal wherein each cycle thereof has first and second portions, and wherein said frequency analyzing means times the first portion of each cycle to determine the frequency of the periodic output signal, and thereby which transducer in the transducer array is to be activated, and then drives the activated transducer with the second portion of each cycle of the periodic waveform.

3. A tactile sensory aid as claimed in claim 2, said periodic output signal comprising a square wave signal having a first "off" portion thereof and a second positive, "on" portion.

4. A tactile sensory aid as claimed in claim 3, said square wave signal having a substantially 50% duty cycle.

5. A tactile sensory aid as claimed in claim 2, said fundamental frequency analyzing means including a shift register having a separate register output for each transducer in said transducer array and being driven by an internal clock, said fundamental frequency analyzing means producing a square wave output signal at the detected fundamental frequency, and said shift register measuring the "off" portion of said square wave output signal, and directing the "on" portion of the square wave output signal to a particular transducer in accordance with the measured "off" portion.

6. A tactile sensory aid as claimed in claim 1, wherein the tactile aid is portable and further includes a portable battery power supply, to be carried by the person, for providing electrical power for said detecting transducer, said fundamental frequency analyzing means, said portable transducer array, and said frequency analyzing means.

7. A tactile sensory aid to be worn by a deaf person for detecting and providing to the person tactile information on the fundamental frequency of detected speech, encoded to provide both frequency of actuation and spatial indications thereof, comprising:

a. a transducer for detecting speech and providing an output speech signal indicative thereof;

b. a fundamental frequency analyzing means receiving said speech signal as an input and providing an output signal representative of the fundamental frequency of the detected speech;

c. a transducer array, to be attached to a tactile-sensitive area of the body of the deaf person, said transducer array defining a geometrical array such that the activation of a particular transducer within the geometrical array provides a spatial indication to the person of the fundamental frequency of the detected speech; and d. a frequency analyzing means, receiving said output signal representative of the fundamental frequency, for detecting the frequency of the output signal and for energizing a particular transducer in the transducer array depending upon the detected frequency, with a signal representative of the fundamental frequency of the detected speech, such that the frequency of actuation of the transducer provides an indication of the fundamental speech frequency, while the location of the particular transducer in the geometric array simultaneously provides a spatial indication of the fundamental speech frequency, said fundamental frequency analyzing means including a shift register having a separate register output for each transducer in said transducer array and being driven by an internal clock, said fundamental frequency analyzing means producing a square wave output signal at the detected fundamental frequency, and said shift register measuring the off portion of the said square wave output signal, and directing the on portion of the square wave output signal to a particular transducer in accordance with the measured off portion.

8. A tactile sensory aid to be worn by a deaf person for detecting and providing to the person tactile information on the fundamental frequency of detected speech, encoded to provide both frequency of actuation and spatial indications thereof, comprising:

b. a fundamental frequency analyzing means receiving said speech signal as an input and providing an output signal representative of the fundamental frequency of the detected speech;

c. a transducer array, to be attached to a tactile-sensitive area of the body of the deaf person, said transducer array defining a geometrical array such that the activation of a particular transducer within the geometrical array provides a spatial indication to the person of the fundamental frequency of the detected speech; and d. a frequency analyzing means, receiving said output signal representative of the fundamental frequency, for detecting the frequency of the output signal and for energizing a particular transducer in the transducer array depending upon the detected frequency, with a signal representative of the fundamental frequency of the detected speech, such that the frequency of actuation of the transducer provides an indication of the fundamental speech frequency, while the location of the particular transducer in the geometric array simultaneously provides a spatial indication of the fundamental speech frequency, said fundamental frequency analyzing means providing a periodic output signal wherein each cycle thereof has first and second portions, and wherein said frequency analyzing means times the first portion of each cycle to determine the frequency of the periodic output signal, and thereby which transducer in the transducer array is to be activated, and then drives the activated transducer with the second portion of each cycle of the periodic waveform.

9. A tactile sensory aid as claimed in claim 8, said periodic output signal comprising a square wave signal having a first "off" portion thereof and a second positive, "on" portion.

10. A tactile sensory aid as claimed in claim 7, said square wave signal having a substantially 50% duty cycle.

* * * * *

UNITED STATES PATENT AND TRADEMARK OFFICE
CERTIFICATE OF CORRECTION

PATENT NO. : 4,581,491

DATED : April 8, 1986

INVENTOR(S) : Arthur Boothroyd

It is certified that error appears in the above-identified patent and that said Letters Patent is hereby corrected as shown below:

Column 5, line 63 (first full sentence) to line 67 (end of second sentence) should read:

--The output of flip-flop 50 is a DC square wave 16, Figures 1 and 3g, and is passed by AC coupling through a capacitor 54 to provide an input for the following stages.--

In the Claims:

Claim 8, before subsection "b." insert

--a. A transducer for detecting speech and providing an output speech signal indicative thereof;--.

Signed and Sealed this

Twenty-seventh Day of January, 1987

Attest:

DONALD J. QUIGG

Attesting Officer

Commissioner of Patents and Trademarks